(12) United States Patent
Sakas et al.

(10) Patent No.: US 8,131,345 B2
(45) Date of Patent: Mar. 6, 2012

(54) COMBINING FIRST AND SECOND IMAGE DATA OF AN OBJECT

(75) Inventors: Georgios Sakas, Darmstadt (DE); Marcus Grimm, Engelsbach (DE)

(73) Assignees: Esaote S.p.A., Casale Monferrato (AL) (IT); Medcom Gesellschaft fur Medizinische Bildverarbeitung MBH, Darnstadt (DE)

( * ) Notice: Subject to any disclaimer, the term of this patent is extended or adjusted under 35 U.S.C. 154(b) by 254 days.

(21) Appl. No.: 11/858,279

(22) Filed: Sep. 20, 2007

(65) Prior Publication Data

US 2008/0009699 A1  Jan. 10, 2008

Related U.S. Application Data

(63) Continuation of application No. 10/815,759, filed on Apr. 2, 2004, now abandoned.

(30) Foreign Application Priority Data

Apr. 11, 2003  (EP) ..................... 03008448

(51) Int. Cl.
*A61B 5/00* (2006.01)

(52) U.S. Cl. ........ 600/427; 382/128; 382/190; 382/294; 382/313; 600/411; 600/443

(58) Field of Classification Search ................... 600/407, 600/410, 417, 426, 427, 437, 438, 440, 411, 600/443; 382/131, 151, 154, 190, 294, 128, 382/313
See application file for complete search history.

(56) References Cited

U.S. PATENT DOCUMENTS

| | | | |
|---|---|---|---|
| 5,531,520 A | 7/1996 | Grimson et al. | |
| 6,351,573 B1* | 2/2002 | Schneider | 382/294 |
| 6,379,302 B1 | 4/2002 | Kessman et al. | |
| 6,546,279 B1 | 4/2003 | Bova et al. | |
| 6,775,404 B1* | 8/2004 | Pagoulatos et al. | 382/154 |
| 2002/0049378 A1 | 4/2002 | Grzeszczuk et al. | |
| 2002/0128550 A1 | 9/2002 | Van Den Brink et al. | |
| 2003/0000535 A1 | 1/2003 | Galloway, Jr. et al. | |
| 2006/0072808 A1 | 4/2006 | Grimm et al. | |
| 2006/0165267 A1* | 7/2006 | Wyman et al. | 382/128 |
| 2006/0257027 A1 | 11/2006 | Hero et al. | |
| 2007/0167801 A1* | 7/2007 | Webler et al. | 600/459 |
| 2009/0022380 A1* | 1/2009 | Zhao et al. | 382/131 |

OTHER PUBLICATIONS

Leonard, "Sensor Fusion for Surgical Applications," 15th Annual aESS/IEEE Dayton Section Symposium. Sensing the World: Analog Sensors and Systems Across the Spectrum, 15th, 1998, New York, NY, pp. 37-44.

Aylward et al., "Intra-operative 3-D Ultrasound Augmentation," Proceedings 2002 IEEE International Symposium on Biomedical Imaging, Washington, DC, Jul. 7, 2002, pp. 421-424.

Porter et al., "Three-Dimensional Registration and Fusion of Ultrasound and MRI Using Major Vessels as Fiducial Markers," IEEE Transactions on Medical Imaging, IEEE Inc., New York, vol. 20, No. 4, Apr. 2001, pp. 354-359.

(Continued)

*Primary Examiner* — Brian Casler
*Assistant Examiner* — Amanda Lauritzen
(74) *Attorney, Agent, or Firm* — Neifeld IP Law, PC

(57) ABSTRACT

A system and method are provided for displaying images of first and second image data in which geometry data is transferred from an ultrasound imaging detector to an image combination device in addition to first image data to reduce the need for calibration and registration.

16 Claims, 3 Drawing Sheets

OTHER PUBLICATIONS

Pagoulatos et al., "A Fast Calibration Method for 3-D Tracking of Ultrasound Images Using a Spatial Localizer," Ultrasound in Medicine and Biology, New York, NY, vol. 27, No. 9, Sep. 2001, pp. 1219-1229.

Pagoulatos et al., "Interactive 3-D Registration of Ultrasound and Magnetic Resonance Images Based on a Magnetic Position Sensor," IEE Transactions on Information Technology in Biomedicine, vol. 3, No. 4, Dec. 1999.

EP search report for 03008448.7, Sep. 23, 2003.

* cited by examiner

COMBINING FIRST AND SECOND IMAGE DATA OF AN OBJECT

CROSS REFERENCE TO RELATED APPLICATIONS

This application is a continuation of application Ser. No. 10/815,759, filed Apr. 2, 2004, now abandoned which claims priority to EP application EP 03008448.7, filed Apr. 11, 2003.

This application incorporates by reference all of the disclosure, including the specification, claims, and figures in application Ser. No. 10/815,759, filed Apr. 2, 2004.

BACKGROUND OF THE INVENTION

The invention relates to an apparatus and a method for/of combining first and second image data of an object. An ultrasound (US) detector repeatedly generates the first image data of the object and the second image data of the object are generated separately. In the apparatus, means for storing and/or receiving the second image data of the object (such as an image data storage and/or an interface) are provided. For example, the second image data may have been recorded earlier by a computer tomography (CT), a magnetic resonance (MR), a positron emission tomography (PET), an X-ray and/or a three-dimensional (3D) US imaging device. In particular, any 3D image information can be used as the second image data. A combination device combines the first and second image data of the object. The combined image data may be displayed in separate areas of a screen and/or may be superimposed on a screen. More particularly, the invention may be applied in the field of stereographic diagnosis concerning human or animal bodies, but also concerning material research and/or material examination.

Ultrasound detectors are comparatively easy to handle and are able to deliver image information quasi-continuously and, approximately, in real-time. However, in many applications, other imaging technologies (such as the ones mentioned above) provide better results. Therefore, it has been proposed earlier to combine image information of better quality, which has been recorded earlier, with real-time ultrasound image information.

In the scientific publication of Pagoulatos et al.: "Interactive 3-D Registration of Ultrasound and Magnetic Resonance Images Based on a Magnetic Position Sensor", published in IEEE TRANSACTIONS ON INFORMATION TECHNOLOGY IN BIOMEDICINE, VOL. 3, NO. 4, December 1999, describes an apparatus of the type mentioned above. It is proposed in the publication to use an MR imaging device and to register the imaging object relative to the MR imaging device. The term "register" means that the geometry of the object and the coordinate system of the MR imaging device are brought into a defined relation. The apparatus comprises a position sensor, which is firmly coupled to an ultrasound probe. Using the position sensor and due to the fact that its relative position to the ultrasound probe does not vary, it is possible to track the position and the orientation of the ultrasound probe. However, it is necessary to calibrate the position sensor relative to the ultrasound probe and to register the imaging object relative to the coordinate system of the ultrasound probe. As a result, the MR imaging information and the ultrasound imaging information can be combined.

Using systems of the type described before, it is possible to display MR image information of the same orientation and/or scaled in the same manner as the most recent US image. In other words: it can be simulated that the MR image is recorded in real-time, provided that the image data processing is fast enough.

However, the various calibration and registration procedures are time-consuming and need to be performed with care in order to obtain good results. For example, the position of a set of landmarks on the surface of the object and/or anatomical markers (in case of a human or animal body) is to be detected during registration.

Furthermore, modern US systems enable the user to vary the penetration depth of the US image in the object and/or to change the ultrasound probe. As a consequence, the calibration of the position sensor relative to the ultrasound probe and the registration of the imaging object relative to the coordinate system of the ultrasound probe are no longer valid.

There are prior art ultrasound devices with pre-calibrated pixel sizes wherein the pixel size can be varied by the user. However, only step-like increases or decreases of the pixel size (or of a spatial dimension of the ultrasound image) can be performed with these prior art devices.

U.S. Pat. No. 6,546,279 B1 discloses a method and an arrangement for locating, vectoring and inserting a needle-like medical device toward and into a targeted patient anatomic feature while the patient is being imaged with multi-modality medical imaging equipment. In the second embodiment of the document at least a portion of the patient is imaged with a first imaging technique (such as computed tomography) to provide a first set of imaging data, which has a fixed frame of reference. Ultrasound imaging data is obtained. The ultrasound imaging data is not fixed relative to the fixed frame of reference. Position data is determined for the ultrasound device. Using the determined position data and the ultrasound imaging data, a converted set of imaging data is provided which is referenced to the fixed frame of reference.

The publication "sensor fusion for surgical applications" by Jim Leonhard (15$^{th}$ Annual AESS/IEEE Dayton Section Symposium. Sensing the world: Analog sensors and systems across the spectrum (Cat. No. 98EX178), pages 37-44, XP002253643, New York, N.Y., USA, IEEE, USA) discloses a surgical navigation system which combines preoperate 3d imagery and intra-operate localisation to register a patient.

US 2002/0128550 A1 discloses a diagnostic imaging system. Magnetic resonance image and ultrasound images are registered in a common reference frame.

It is an object of the present invention to provide an apparatus and a method of the type indicated above, which allow lessening the effects of the disadvantages mentioned before, which facilitate the handling by the user and which allow using a greater variety of features of the ultrasound system without loosing time for calibration and/or registration. In particular, it is desirable to adjust the settings of the ultrasound system and/or to change the ultrasound probe and to continue with the ultrasound imaging process without interruption.

SUMMARY OF THE INVENTION

A method is provided of combining first and second image data of an object, wherein the first image data of the object are repeatedly generated by an ultrasound detector, wherein the second image data of the object are generated separately, wherein the first image data are transferred from the ultrasound detector to a combination device and wherein the combination device is adapted to combine the first and second image data of the object. Geometry data is transferred in addition to the first image data from the ultrasound detector to the combination device.

In particular, the geometry data comprise information for establishing a link between the geometry of the first image data and the geometry of the second image data.

Preferably, the geometry data are transferred directly from the ultrasound detector to the combination device, e.g. via an additional cable which connects the detects and the device.

Further, an apparatus is provided for combining first and second image data of an object, the apparatus comprising an ultrasound detector for repeatedly generating the first image data of the object; means for storing and/or receiving the second image data of the object; a combination device which is adapted to combine the first and second image data of the object; and an image data connection from the ultrasound detector to the combination device for transferring the first image data. The ultrasound detector is connected to the combination device by a geometry data connection, wherein the geometry data connection, the ultrasound detector and the combination device are adapted to transfer geometry data additionally to the first image data from the ultrasound detector to the combination device.

The geometry data may, for example, comprise information for establishing a link between the geometry of the first image data and the geometry of the second image data. The "link" (or, in other words, a processable relation between the first and the second image data) allows, for example, the determination of an overlapping region of a first image represented by the first image data and of a second image represented by the second image data. According to a preferred application, the combination device continuously displays a first image of the object corresponding to the repeatedly generated first image data and continuously displays a second image of the object corresponding to the second image data, wherein the orientation and/or scaling of at least a part of the object is identical in the first and in the second image. In particular, the second image data may be displayed, as if the second image data have repeatedly been recorded instead of or in addition to the first image data.

As a consequence of the fact that the geometry data are available to the combination device, the effort for re-calibrating the ultrasound detector relative to a tracking sensor (if any) and/or for re-registrating the object relative to the coordinate system of the ultrasound detector can be reduced or eliminated.

The geometry data may comprise one or more than one of the following type of information. In particular, any combination and/or aggregation of the following type of information can be included in the geometry data:

a) information concerning at least one spatial dimension of an image unit of the first image data, in particular of a pixel (preferably separately for different directions of a coordinate system);

b) information concerning an image position of at least a part of an image, which is represented by the first image data, relative to a reference point of the ultrasound detector or relative to a reference point or reference object in the ultrasound image. This information is particularly useful, if a user can adjust a zoom factor of the ultrasound image. For example, this information comprises a distance in image units (e.g. pixels). In combination with the scaling information of item a), the distance may be defined in cm or another unit of length;

c) information concerning an orientation of the ultrasound image relative to a reference point or a reference object of the ultrasound detector (in particular an ultrasound probe of the detector). For example, this information may comprise the orientation of at least one axis of a coordinate system of the ultrasound image;

d) information concerning a region or an area, which is actually covered by an ultrasound image that is represented by the first image data; and e) information concerning a detector position of the ultrasound detector relative to a position sensor for determining a location and/or an orientation of the ultrasound detector. Instead of or in addition to a position sensor, a signal source may be coupled to the ultrasound probe, wherein the signal can be evaluated in order to determine the position of the probe. For example, such information may be collected once in advance and may be saved individually for each ultrasound probe, which can be connected to the ultrasound system/device. In this case, it is sufficient during operation to transfer simply an identification signal, which enables to identify the probe that is used. The combination device can select the respective geometry information using the identification information. In a specific embodiment, the information concerning the relative position, which is transferred or saved, may be a calibration matrix.

Preferably, all of these types of information are transferred from the ultrasound detector to the combination device.

Since information concerning at least one spatial dimension of an image unit of the first image data (e.g. the pixel size) can be transferred from the ultrasound device to the combination device, according to one embodiment of the present invention, the user can choose the spatial dimension within the respective range of the ultrasound device. Consequently, a continuously adjustable pixel size can be implemented in the ultrasound device.

The information concerning an image position relative to a reference point of the ultrasound detector facilitates the combination of the two different types of image data and makes it possible to adjust the position of the ultrasound image, for example by using a control knob provided at the ultrasound probe.

The information concerning an orientation of the ultrasound image relative to a reference point of the ultrasound detector enable the user to change the orientation by operating a control element at the ultrasound probe.

Similarly to the information concerning the pixel size, the information concerning a region or an area, which is actually covered by an ultrasound image facilitates the combination of the ultrasound image data with the other image data.

According to a preferred embodiment at least a part of the geometry data is repeatedly transferred to the combination device, in particular every time when the first image data are generated and/or when the first image data are transferred to the ultrasound detector. The geometry data may be transferred on request and/or without request from the combination device and/or from another part or unit (for example of a central control unit) of the apparatus.

There are further possibilities to use the additional data connection between the ultrasound detector and the combination device, or to use a further data connection. For example, a mode and/or a user setting of the ultrasound detector may be transferred from the ultrasound detector to the combination device, on request or without request of the combination device or another unit of the apparatus. E.g. a colour of the ultrasound image to be used in displaying the ultrasound image, a repetition frequency of the ultrasound image generation (for example in order to give an indication to the user, if the frequency is too low) and/or information representing the object may be transferred.

If the ultrasound detector comprises a control unit for controlling an image data generation of the ultrasound detector, the control unit may be adapted to generate at least a part of the geometry data. For example, the control unit can adjust a penetration depth of the ultrasound image, using a velocity value of the ultrasound waves in the object, by setting a time limit for detection of US echo signals. In this case, the control unit can calculate the penetration depth and can transfer information about the penetration depth to the combination device. Further, the width of an image recording area of an ultrasound probe may be available to the control unit for control purposes and the control unit can transfer this information to the combination device.

In a preferred embodiment of the apparatus the image data connection is adapted to directly transfer the first image data in a digital format from the ultrasound detector to the combination device. This saves time for transferring the first image data and reduces costs and effort of the apparatus. Furthermore, the ultrasound detector, the combination device and (optionally) further parts or units of an imaging system may be integrated in one and the same device. For example, several or all of the units of such a device may be connected to a data bus system for transferring data.

Generally, the image data connection and/or the geometry data connection may be realised by a data bus (e.g. USB or FireWire, IEEE 1394) and/or may be part of a data network. Preferably, the embodiment of the connection or connections shall allow displaying a first image (represented by the first image data) and a second image (represented by the second image data) approximately in real-time of the generation of the first image data, for example within less than 100 ms after the generation. Ultrasound is particularly useful in order to generate the first image data, since the generation process can be performed with high repetition frequency (quasi-continuously). The corresponding data connection and the following data processing should not delay the displaying in way, which can be noticed by the user.

BRIEF DESCRIPTION OF THE DRAWINGS

In the following, examples and possible further features of the invention are described by way of reference to the accompanied drawing. The embodiment shown in the FIGS. 1 to 3 and 5 represent the currently known best mode of the invention. However, the invention is not limited to the features described in the following description. The figures of the drawing schematically show.

DETAILED DESCRIPTION

Figure 1:
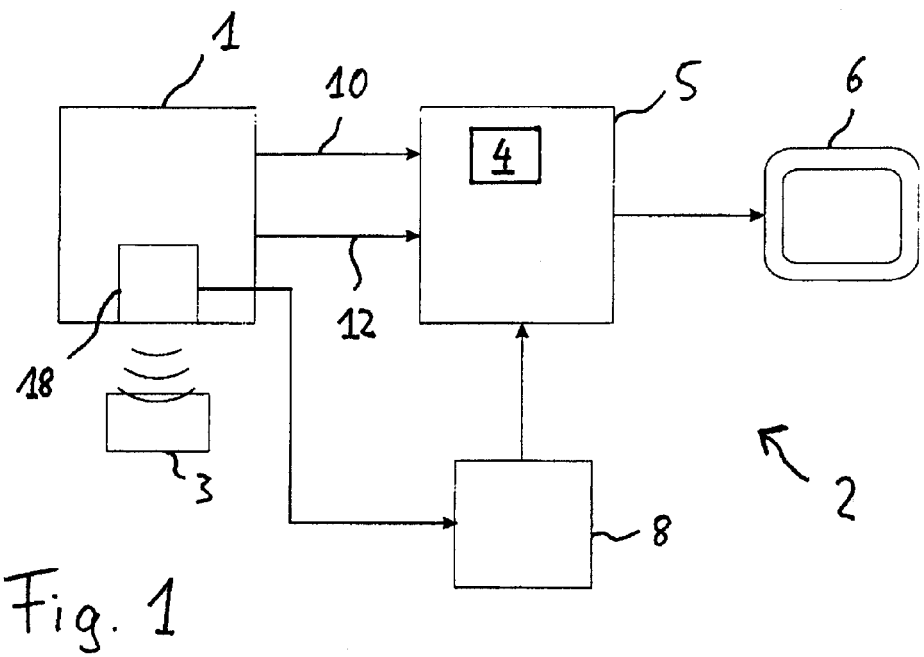
FIG. 1 an arrangement 2 comprising an apparatus for combining ultrasound image data with a second type of data, e.g. CT image data.

Images of an object 3 (shown in FIG. 1) are to be displayed on a screen 6. An ultrasound detector 1 generates first image data of the object 3 and transfers the first image data to a combination device 5 via an image data connection 10. The combination device 5 comprises a data storage 4, which contains second image data that have previously been generated by a separate device (not shown in FIG. 1). The combination device 5 is adapted to combine the first and second image data and to display them on a screen 6, which is connected to the combination device 5. For example, the first and second image data may be displayed separately on a split screen or may be superimposed. In any case, it is preferred that a first image, which is generated using the first image data, and a second image, which is generated using the second image data, precisely show at least partially the same area or region of the object 3 in the same orientation (angle of view) and scaling (dimensions).

The ultrasound detector 1 and the combination device 5 are connected to each other by an additional data connection 12 for transferring geometry data from the ultrasound detector 1 to the combination device 5. In particular, the geometry data connection 12 may be connected (as shown in FIG. 2) to a control unit 14 of the ultrasound detector 1.

In practice, the data connections 10, 12 may be realised by separate data connection links or by the same data connection link. For example, a "link" may comprise a connection line, a plurality of connection lines and/or a digital data bus or bus system.

An ultrasound probe 16 (FIG. 2) of the ultrasound detector 1 is firmly coupled to a position sensor 18 of a tracking system. The determination of the orientation and the location of such a position sensor and, thereby, of the ultrasound probe is known in the art (see the above-cited publication of Pagoulatos et al.). For example, magnetic and/or optical (e.g. infrared) signals may be used by the tracking system. The position sensor 18 is connected to a tracking system control unit 8 and the control unit 8 is connected to the combination device 5. During operation of the arrangement 2, the control unit 8 repeatedly or quasi-continuously transfers information concerning the position and concerning the orientation of the ultrasound probe 16 to the combination unit 5. Alternatively, this information may be transferred from the US detector to the combination device. I.e. this information might be at least partially included in the geometry data, which are transferred.

Figure 2:
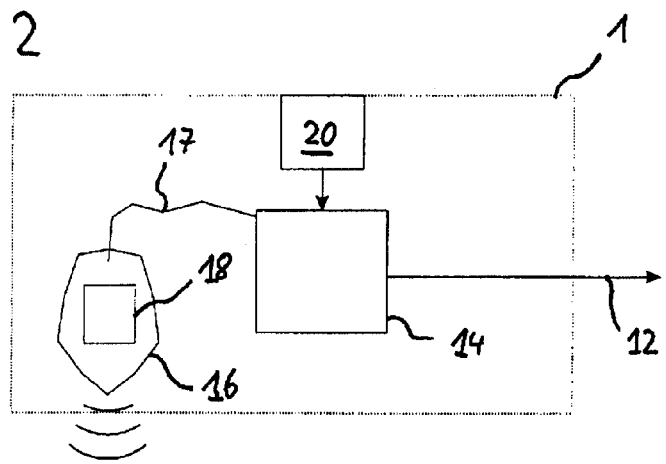
FIG. 2 a more detailed view of the ultrasound detector shown in FIG. 1.

As shown in FIG. 2, the ultrasound device 1 may, for example, comprise an ultrasound probe 16, which is connected to the ultrasound control unit 14 via a flexible cord 17 for transferring echo signals to the control unit 14. On the other hand, the control unit 14 transfers control signals to the ultrasound probe via the cord 17. Also, it is possible that at least a part of the geometry information is transferred from the ultrasound probe 16 to the control unit 14 and/or that at least a part of the geometry information generated by the control unit 14 is based on and/or derived from information, which is transferred from the ultrasound probe 16 to the control unit 14. For example, the ultrasound probe 16 may be replaced and, therefore, transfers information concerning its identity to the combination device 5. In the combination device 5, in an additional unit of the arrangement 2, and/or in the combination device 5, information concerning the relative position and/or orientation of the specific ultrasound probe 16 relative to the position sensor 18 may be saved. For example, the ultrasound probe 16 may comprise a clip for attaching the position sensor 18. Therefore, it is possible to precisely position and orientate the position sensor 18 relative to the ultrasound probe 16 and to determine as well as to save the respective geometry data in advance. After replacement of the ultrasound probe 16, the identity information and the saved geometry information can be combined. As a consequence, it is not necessary to re-calibrate the arrangement consisting of the ultrasound detector 1 and the position sensor 18.

An input unit 20 is connected to the ultrasound control unit 14, for example for inputting settings of the ultrasound detector, such as a penetration depth or range of the ultrasound image. Further, the user may change the orientation of the ultrasound image via the input unit 20.

According to a preferred embodiment of the invention, the ultrasound image data are generated from analog signals in a unit 22 of the ultrasound detector. The unit 22 may, for example, be controlled by the control unit 14 (as shown in the figure), be a part of the control unit 14 or be realised by a combination of the ultrasound probe 16 and the control unit 14. The unit 22 is connected to an A/D-converter 24, which converts the analog image signal to a digital image signal. The A/D-converter 24 is connected to an image data processing unit 26, which is also connected to the control unit 14 or to an alternative unit of the ultrasound detector that transfers geometry information to the image data processing unit 26. Thus, the image data processing unit 26 can combine the geometry information with the image data and/or can transferred both information/data to a further unit (not shown in FIG. 3). For example, the image data processing unit 26 may be identical to or part of the combination device 5. In this case, the image data processing unit 26 also combines the first and second image information and the unit 26 may be connected to a screen 6 (as shown in the figure).

Figure 3:
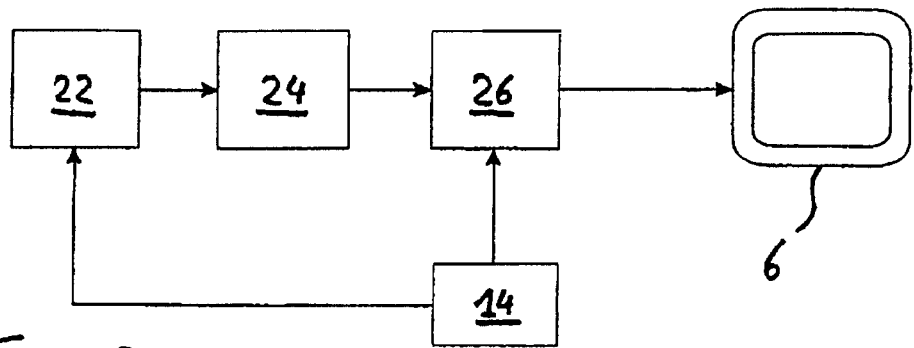
FIG. 3 a first example of an arrangement of components, which contribute to a processing of the ultrasound image data.

The embodiment of FIG. 3 is of particular advantage, if the ultrasound detector and the combination device are integrated in one device.

In an alternative arrangement, the ultrasound detector may directly generate digital image data, without conversion from analog to digital.

Figure 4:
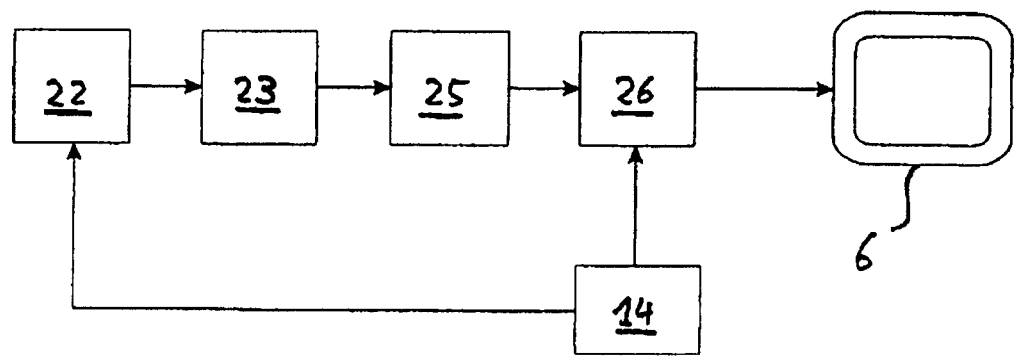
FIG. 4 a second example of an arrangement of components, which contribute to a processing of the ultrasound image data.

An alternative arrangement is shown in FIG. 4. The same reference numeral denote units or devices having the same or a corresponding function. A D/A-converter 23 converts the digital image signal received via a connection from the unit 22 or from a corresponding unit to an analog image signal, for example to a signal in standard video format. An A/D-converter 25 that may be part of the combination device (e.g. a video capture card) is connected to the unit 23. The unit 25 converts the analog signal to a digital signal, e.g. in pixel format. Then, the unit 26 processes the digital signal.

Figure 5:
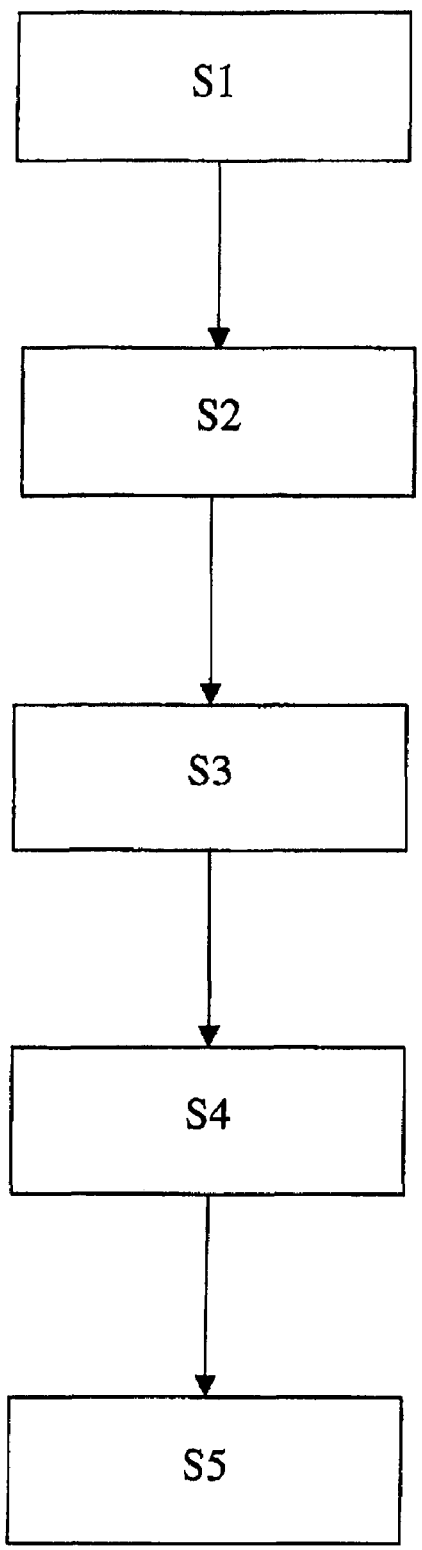
FIG. 5 a flow-chart of processing image data.

An example of processing and combining ultrasound image information is described in the following with reference to FIG. 5.

In step S1, geometry information concerning the scaling of the ultrasound image information are combined with the ultrasound image information. For example, the ultrasound image data contains information concerning the intensity of image units (e.g. pixels) before step S1, but no information concerning the dimension of the image units. The dimensional information is added by performing step S1.

In step S2, calibration information concerning the relative position of the ultrasound detector to the position sensor is added and/or combined with the information resulting from step S1. The calibration information may comprise as well information concerning the orientation of the ultrasound image, which may be changed by the user. As a result, it is now possible to identify the orientation and location of specific areas of the ultrasound image.

In step S3, the geometry information concerning the registration of the object within the coordinate system of the ultrasound system or the tracking system is added.

In step S4, the ultrasound image data resulting from step S3 can be combined with the second image data.

In practice, at least some of the processing operations of steps S1 to S4 may be realised by performing a polygon scanline method, which is described for example in the book "Computer Graphics. Principles and Practice." by James D. Foley, Andries VanDam, Steven K. Feiner, published by Addison-Wesley, Boston, U.S.A. The combination device 5 shown in FIG. 1 may perform the data processing, for example.

For example, it is first calculated whether an overlapping region of the respective images exists. If this is the case, the corresponding overlapping region of the second image data is read out from the data storage and is prepared for displaying (step S5). The corresponding data of the second image data are processed before displaying so that the second image, which is based on the second image data, can be displayed in the same orientation and scaling as the ultrasound image.

The procedure described before is preferred, if the ultrasound image is two-dimensional. For 3D-ultrasound image information it is as well possible, to choose the orientation (i.e. the angle of the view) of the ultrasound image to be shown, in particular to adapt the orientation according to other criteria. In any case, it is possible to adapt the scaling of the ultrasound image before displaying. Instead of, or additionally to displaying, the combined first and second image information may be processed in another way. For example, they can be stored and/or evaluated in a different manner.

The invention claimed is:

1. A method for displaying in an image combination device images of an object, comprising:
   storing, in said image combination device, second image data of an object from which said image combination device can generate second images of said object, said second image data obtained from a second imaging system;
   repeatedly transferring, from an ultrasound imaging detector of an ultrasound image detector system to said image combination device, first image data of said object;
   a user changing a zoom factor of said ultrasound imaging detector within an adjustable range for zoom factor of said ultrasound imaging detector from an old zoom factor to a new zoom factor;
   said ultrasound imaging detector responding to said user changing said zoom factor from said old zoom factor to said new zoom factor by transferring from said ultrasound imaging detector to said image combination device spatial dimension data defining spatial dimension of an image unit of said first image data corresponding to said new zoom factor; and
   determining, using said image combination device, spatial dimension data of said image unit for said first data corresponding to said old zoom factor and said new zoom factor, a new scale for display of said second images; and
   displaying, in said image combination device, a second image of said second image data displayed at said new scale.

2. The method of claim 1 wherein said image unit is a pixel and said spatial dimension of an image unit of said first image data is a spatial dimension associated with said pixel.

3. The method of claim 1 further comprising:
   maintaining constant at least scale, between concurrently displayed images of said object displayed from said first image data and images of said object displayed from said second image data.

4. The method of claim 1 further comprising transferring from said ultrasound image detector system to said image combination device data indicating position of said ultrasound imaging detector relative to a position sensor.

5. The method of claim 1 further comprising:
   determining, in said ultrasound image detector system, a width of an image recording area; and
   transmitting said width to said image combination unit.

6. The method of claim 1 wherein said ultrasound image detector system transfers to said image combination device spatial dimension data indicating spatial dimension of an image unit of said first image data each time said ultrasound image detector system transfers first image data to said image combination device.

7. The method of claim 1 wherein said ultrasound imaging detector provides a continuously adjustable pixel size.

8. The method of claim 1, wherein subsequently to said user changing said zoom factor from said old zoom factor to said new zoom factor, first image data of said object corresponding to said new zoom factor are transferred from said ultrasound imaging detector to said image combination device.

9. A method for displaying in an image combination device images of an object, comprising:
    storing, in said image combination device, second image data of an object from which said image combination device can generate second images of said object, said second image data obtained from a second imaging system;
    repeatedly transferring, from an ultrasound imaging detector of an ultrasound image detector system to said image combination device, first image data of said object;
    a user changing an orientation value of an orientation control element in said ultrasound imaging detector from an old orientation value to a new orientation value, thereby changing orientation of first image data transmitted from said ultrasound imaging detector to said image combination device, such that orientation of an image of said object relative to orientation of said ultrasound imaging detector changes from an old orientation to a new orientation;
    said ultrasound imaging detector responding to said user changing said orientation value, by transferring said orientation value from said ultrasound imaging detector to said image combination device;
    determining, using said image combination device change in orientation of said first image relative to orientation of said ultrasound imaging detector from said old orientation to said new orientation, based upon change in said orientation value received from said ultrasound imaging detector;
    changing an orientation of said second image data to a changed orientation corresponding to said change in orientation of said first image; and
    displaying, in said image combination device, said second images of said object with said changed orientation.

10. The method of claim 9 further comprising transferring from said ultrasound imaging image detector system to said image combination device data indicating position of said ultrasound imaging detector relative to a position sensor.

11. The method of claim 9 further comprising:
    determining, in said ultrasound image detector system, a width of an image recording area; and
    transmitting said width to said image combination unit.

12. The method of claim 9 wherein said ultrasound image detector system transfers to said image combination device change in orientation each time said ultrasound image detector system transfers first image data to said image combination device.

13. The method of claim 9, wherein subsequently to said user changing said orientation value from said old orientation value to said new orientation value, first image data of said object corresponding to said new orientation value are transferred from said ultrasound imaging detector to said image combination device.

14. A system for displaying in an image combination device images of an object, comprising:
    an image combination device:
    said image combination device designed to store second image data of an object;
    said image combination device designed to generate second images of said object, wherein said second image data were from a second imaging system;
    an ultrasound image detector system comprising an ultrasound imaging detector;
    a data communication link between said ultrasound image detector system and said image combination device designed to transfer from an ultrasound imaging detector to said image combination device first image data of said object;
    said ultrasound imaging detector having a zoom control for an adjustable range for zoom factor, designed to enable a user to change a zoom factor of said ultrasound imaging detector from an old zoom factor to a new zoom factor;
    said ultrasound imaging detector designed to respond to said user changing said zoom factor from said old zoom factor to said new zoom factor by transferring from said ultrasound imaging detector to said image combination device spatial dimension data defining spatial dimension of an image unit of said first image data corresponding to said new zoom factor; and
    said image combination device designed to determine a new scale for display of said second images, based upon said spatial dimension data of said image unit for said first data corresponding to said old zoom factor and said new zoom factor; and
    said image combination device designed to display a second image of said second image data at said new scale.

15. The method of claim 14 wherein said ultrasound imaging detector provides a continuously adjustable pixel size.

16. A system for displaying in an image combination device images of an object, comprising:
    said image combination device, wherein:
    said image combination device stores second image data of an object from which said image combination device can generate second images of said object, said second image data obtained from a second imaging system;
    an ultrasound image detector system comprising an ultrasound imaging detector;
    a data communication link between said ultrasound image detector system and said image combination device designed to transfer from an ultrasound imaging detector to said image combination device first image data of said object;
    said ultrasound imaging detector having an orientation control element for controlling orientation of image data provided by said ultrasound imaging detector, such that changing said orientation value of said orientation control unit from an old orientation value to a new orientation value changes orientation of first image data transmitted from said ultrasound imaging detector to said image combination device, such that orientation of an image of said object relative to orientation of said ultrasound imaging detector changes from an old orientation to a new orientation;
    said ultrasound imaging detector designed to respond to said user changing said orientation value from said old orientation value to said new orientation value, by transferring said new orientation value from said ultrasound imaging detector to said image combination device;

said image combination device designed to change orientation of said second image data to a changed orientation corresponding to said change in orientation of said first image from said old orientation value to said new orientation value; and said image combination device designed to display said second images of said object with said changed orientation.

* * * * *